US006406435B1

(12) United States Patent
Mault

(10) Patent No.: US 6,406,435 B1
(45) Date of Patent: Jun. 18, 2002

(54) METHOD AND APPARATUS FOR THE NON-INVASIVE DETERMINATION OF CARDIAC OUTPUT

(76) Inventor: James R. Mault, 1580 Blakcomb Ct., Evergreen, CO (US) 80439

(*) Notice: Subject to any disclaimer, the term of this patent is extended or adjusted under 35 U.S.C. 154(b) by 0 days.

(21) Appl. No.: 09/674,898
(22) PCT Filed: Nov. 17, 1999
(86) PCT No.: PCT/US99/27297
§ 371 (c)(1),
(2), (4) Date: Nov. 7, 2000
(87) PCT Pub. No.: WO00/28881
PCT Pub. Date: May 25, 2000

Related U.S. Application Data
(60) Provisional application No. 60/108,790, filed on Nov. 17, 1998.

(51) Int. Cl.[7] .................................................. A61B 5/08
(52) U.S. Cl. ....................... 600/532; 600/538; 600/437
(58) Field of Search ............................... 600/532, 531, 600/533, 538, 526, 437

(56) References Cited

U.S. PATENT DOCUMENTS

| 2,630,798 A | 3/1953 | White et al. |
| 2,826,912 A | 3/1958 | Kirtz |
| 2,831,348 A | 4/1958 | Kritz |

(List continued on next page.)

FOREIGN PATENT DOCUMENTS

| DE | 198 10 476 | * | 9/1998 |
| EP | 0459647 A2 | | 5/1991 |
| EP | 0 712 638 | * | 12/1995 |
| GB | 2323292 | * | 9/1998 |
| WO | WO 96/40340 | * | 12/1996 |

OTHER PUBLICATIONS

Medical Progress Through Technology, vol. 9, No. 1, 1982 Berlin (D), pp. 27–32, R. Salminen et al., "Computerized Breath–By Breath Analysis of Respiratory Variables During Exercise."

British Journal of Anaesthesia, vol. 49, 1977 London (GB) pp. 575–587, J. A. Bushman et al. "Closed Circuit Anaesthesia."

IEEE Transactions on Biomedical Engineering, vol. 35, No. 9, Sep. 1988, pp. 653–659, Capek et al., "Noninvasive Measurement of Cardia Output Using Partial CO2 ReBreathing."

Clinics in Chest Medicine (Review), vol. 10, 1989, pp. 255–264, Heigenhauser et al., "Measurement if Cardiac Output by Carbon Dioxide ReBreathing Methods."

Determination Of Nitric Oxide Levels By Fluoresence Spectroscopy, Gabor G. and Allon, N. in Biochemical, Pharmacological, and Clinical Aspects of Nitric Oxide, edited by B. A. Weissman et al, Plenum Press, New York, 1995, p. 57.

Primary Examiner—Kevin Shaver
Assistant Examiner—Navin Natnithithadha
(74) Attorney, Agent, or Firm—Gifford, Krass, Groh, Sprinkle, Anderson & Citkowski, P.C.

(57) ABSTRACT

A method and apparatus for the non-evasive determination of the cardiac output of a subject by causing the subject to inhale and exhale air via a respiratory tube in a plurality of breathing cycles including normal breathing cycles in which the inhaled air does not receive any significant amount of exhaled air from the preceding cycle, and rebreathing cycles in which the inhaled air receives an end tidal portion of the exhaled air from the preceding cycle, propagating ultrasonic pulses through the air passing through the respiratory tube and computing the flow volume through the tube from the measured transit times of the pulses and determining the carbon dioxide content in the exhaled air during both the normal breathing cycles and the rebreathing cycles to determine the cardiac output of the subject.

19 Claims, 2 Drawing Sheets

U.S. PATENT DOCUMENTS

| | | | |
|---|---|---|---|
| 2,838,399 A | 6/1958 | Vogel, Jr. | |
| 2,869,357 A | 11/1959 | Kritz | |
| 2,911,825 A | 11/1959 | Kritz | |
| 2,920,012 A | 1/1960 | Sanders et al. | |
| 3,213,684 A | 10/1965 | Seaton et al. | |
| 3,220,255 A | 11/1965 | Scranton et al. | |
| 3,250,270 A | 5/1966 | Bloom | |
| 3,306,283 A | 2/1967 | Arp | |
| 3,523,529 A | 8/1970 | Kissen | |
| 3,527,205 A | 9/1970 | Jones | |
| 3,681,197 A | 8/1972 | Smith | |
| 3,726,270 A | 4/1973 | Griffis et al. | |
| 3,799,149 A | 3/1974 | Rummel et al. | |
| 3,814,091 A | 6/1974 | Henkin | |
| 3,834,375 A | 9/1974 | Sanctuary et al. | |
| 3,895,630 A | 7/1975 | Bachman | |
| 3,938,551 A | 2/1976 | Henkin | |
| 3,962,917 A | 6/1976 | Terada | |
| 3,979,480 A | 9/1976 | Williams | |
| 4,003,396 A | 1/1977 | Fleischmann | |
| 4,051,847 A | 10/1977 | Henkin | |
| 4,078,554 A | 3/1978 | Lemaitre et al. | |
| 4,083,367 A * | 4/1978 | Portner et al. | 600/504 |
| 4,186,735 A | 2/1980 | Henneman et al. | |
| 4,188,946 A | 2/1980 | Watson et al. | |
| 4,197,857 A | 4/1980 | Osborn | |
| 4,200,094 A | 4/1980 | Gedeon et al. | |
| 4,211,239 A | 7/1980 | Raemer et al. | |
| 4,221,224 A | 9/1980 | Clark | |
| 4,230,108 A * | 10/1980 | Young | |
| 4,341,867 A | 7/1982 | Johansen | |
| 4,359,057 A | 11/1982 | Manzella | |
| 4,368,740 A | 1/1983 | Binder | |
| 4,386,604 A | 6/1983 | Hershey | |
| 4,425,805 A | 1/1984 | Ogura et al. | |
| 4,440,177 A | 4/1984 | Anderson et al. | |
| 4,444,201 A | 4/1984 | Itoh | |
| 4,456,016 A * | 6/1984 | Nowacki et al. | 600/538 |
| 4,463,764 A | 8/1984 | Anderson et al. | |
| 4,538,620 A * | 9/1985 | Nowacki et al. | 600/538 |
| 4,572,208 A | 2/1986 | Cutler et al. | |
| 4,598,700 A | 7/1986 | Tamm | |
| 4,608,995 A | 9/1986 | Linnarsson et al. | |
| 4,619,269 A | 10/1986 | Cutler et al. | |
| 4,648,396 A | 3/1987 | Raemer | |
| 4,658,832 A | 4/1987 | Brugnoli | |
| 4,753,245 A | 6/1988 | Gedeon | |
| 4,756,670 A | 7/1988 | Arai | |
| 4,781,184 A | 11/1988 | Fife | |
| 4,796,639 A | 1/1989 | Snow et al. | |
| 4,850,371 A | 7/1989 | Broadhurst et al. | |
| 4,856,531 A | 8/1989 | Merilainen | |
| 4,909,259 A | 3/1990 | Tehrani | |
| 4,914,959 A | 4/1990 | Mylvaganam et al. | |
| 4,917,108 A | 4/1990 | Mault | |
| 4,955,946 A | 9/1990 | Mount et al. | |
| 4,986,268 A | 1/1991 | Tehrani | |
| 4,998,018 A | 3/1991 | Kurahashi et al. | |
| 5,022,406 A | 6/1991 | Tomlinson | |
| 5,038,773 A | 8/1991 | Norlien et al. | |
| 5,038,792 A | 8/1991 | Mault | |
| 5,042,500 A | 8/1991 | Norlien et al. | |
| 5,042,501 A | 8/1991 | Kenny et al. | |
| 5,060,506 A | 10/1991 | Douglas | |
| 5,060,655 A | 10/1991 | Rudolph | |
| 5,060,656 A | 10/1991 | Howard | |
| 5,069,220 A | 12/1991 | Casparie et al. | |
| 5,072,737 A | 12/1991 | Goulding | |
| 5,081,871 A | 1/1992 | Glaser | |
| 5,095,900 A | 3/1992 | Fertig et al. | |
| 5,095,913 A | 3/1992 | Yelderman et al. | |
| 5,117,674 A | 6/1992 | Howard | |
| 5,119,825 A | 6/1992 | Huhn | |
| 5,178,155 A | 1/1993 | Mault | |
| 5,179,958 A | 1/1993 | Mault | |
| 5,214,966 A | 6/1993 | Delsing | |
| 5,233,996 A | 8/1993 | Coleman et al. | |
| 5,282,473 A | 2/1994 | Braig et al. | |
| 5,285,794 A | 2/1994 | Lynch | |
| 5,293,875 A | 3/1994 | Stone | |
| 5,299,579 A | 4/1994 | Gedeon et al. | |
| 5,303,712 A | 4/1994 | Van Duren | |
| 5,309,921 A | 5/1994 | Kisner et al. | |
| 5,326,973 A | 7/1994 | Eckerbom et al. | |
| 5,355,879 A * | 10/1994 | Brain | |
| 5,357,972 A | 10/1994 | Norlien | |
| 5,363,857 A | 11/1994 | Howard | |
| 5,398,695 A | 3/1995 | Anderson et al. | |
| 5,402,796 A | 4/1995 | Packer et al. | |
| 5,419,326 A | 5/1995 | Harnoncourt | |
| 5,425,374 A | 6/1995 | Ueda et al. | |
| 5,450,193 A | 9/1995 | Carlsen et al. | |
| 5,468,961 A * | 11/1995 | Gradon et al. | |
| 5,503,151 A | 4/1996 | Harnoncourt et al. | |
| 5,570,697 A * | 11/1996 | Walker et al. | |
| 5,632,281 A | 5/1997 | Rayburn | |
| 5,645,071 A * | 7/1997 | Harnoncourt et al. | |
| 5,647,370 A | 7/1997 | Harnoncourt | |
| 5,676,132 A | 10/1997 | Tillotson et al. | |
| 5,705,735 A * | 1/1998 | Acorn | |
| 5,754,288 A | 5/1998 | Yamamoto et al. | |
| 5,789,660 A * | 8/1998 | Kofoed et al. | |
| 5,796,009 A | 8/1998 | Delsing | |
| 5,800,360 A | 9/1998 | Kisner et al. | |
| 5,816,246 A | 10/1998 | Mirza | |
| 5,831,175 A | 11/1998 | Fletcher-Haynes | |
| 5,834,626 A | 11/1998 | DeCastro et al. | |
| 5,836,300 A * | 11/1998 | Mault | |
| 5,922,610 A | 7/1999 | Alving et al. | |
| 5,932,812 A | 8/1999 | Delsing | |
| 5,957,858 A | 9/1999 | Micheels et al. | |
| 6,010,459 A | 1/2000 | Silkoff et al. | |
| 6,044,843 A | 4/2000 | O'Neil et al. | |
| 6,102,868 A * | 8/2000 | Banner et al. | 600/484 |
| 6,135,107 A * | 10/2000 | Mault | 600/529 |
| 6,174,289 B1 * | 1/2001 | Binder | 600/538 |
| 6,217,524 B1 * | 4/2001 | Orr et al. | 600/504 |
| 6,238,351 B1 * | 5/2001 | Orr et al. | 600/532 |

* cited by examiner

METHOD AND APPARATUS FOR THE NON-INVASIVE DETERMINATION OF CARDIAC OUTPUT

RELATED APPLICATIONS

The present application claims the benefit of provisional application Ser. No. 60/108,790, filed Nov. 17, 1998.

FIELD AND BACKGROUND OF THE INVENTION

The present invention relates to a method and apparatus for the non-invasive determination of the cardiac output of a subject, and particularly to a method and apparatus which utilizes a gas analysis of the air flow through a respiratory device to determine cardiac output, as well as other physiological conditions of a subject, such as oxygen consumption, carbon dioxide production, etc.

U.S. Pat. Nos. 5,038,792; 5,178,155 and 5,179,958, all by the same inventor as the present application, relate to systems for measuring metabolism and related respiratory parameters, such as oxygen consumption and carbon dioxide production through indirect calorimetry using a respiratory gas analyzer device measuring metabolic activity of the subject. My patent application Ser. No. 814,677, filed Mar. 11, 1997, now U.S. Pat. No. 5,836,300, discloses such a respiratory gas analyzer for measuring, not only the metabolic activity of a subject, but also the cardiac output of the subject in a non-invasive manner. The systems described in the above patents employ bi-directional flow meters which pass both the inhalations and the exhalations of the subject breathing through the device, and integrate the resulting instantaneous flow signals to determine total full flow volumes. The concentration of carbon dioxide generated by the subject may be determined by passing the exhaled volume through a carbon dioxide scrubber before it is passed through the flow meter so that the difference between the inhaled and exhaled volumes is essentially a measurement of the carbon dioxide contributed by the lungs. Alternatively, the concentration of carbon dioxide may be determined by measuring the instantaneous carbon dioxide content of the exhaled volume with a capnometer, and integrating that signal with the exhaled flow volume. The oxygen consumption can then be calculated by subtracting the carbon dioxide content from the exhaled volume, and then subtracting the resulting exhaled volume from the inhaled volume.

The systems described in the above-cited patents generally use a scrubber for removing the carbon dioxide in order to permit a determination to be made of the carbon dioxide content of the air, particularly the exhaled air. Such scrubbers, however, are relatively bulky and require replenishment after extended use. In addition, some of the described systems required capnometers for measuring the carbon dioxide concentration. Such capnometers have to be highly precise, and are therefore very expensive, because any errors in measurement of the carbon dioxide content of the exhalations produces a substantially higher error in the resulting determination of the oxygen content, or the carbon dioxide content, of the exhalation.

OBJECTS AND BRIEF SUMMARY OF THE PRESENT INVENTION

One object of the present invention is to provide a method and apparatus which enable the use of such a respiratory gas analyzer for the non-invasive determination of the cardiac output of a subject, as well as for the measurement of oxygen consumption and/or carbon dioxide production.

Another object of the present invention is to provide a method and apparatus for the non-invasive determination of the cardiac output of a subject, which method and apparatus do not require a scrubber for removing the carbon dioxide from the air volume.

A further object of the invention is to provide such a method and apparatus which do not require a capnometer for sensing the carbon dioxide content, but which could include such a capnometer in order to improve accuracy.

A still further object of the invention is to provide such a method and apparatus which may also be used for determining oxygen consumption, and/or carbon dioxide production, as well as other metabolic or cardiovascular conditions.

According to one aspect of the present invention, there is provided a method for the non-invasive determination of the cardiac output of a subject by:

(a) causing the subject to inhale and exhale air via a respiratory tube in a plurality of breathing cycles including normal breathing cycles in which the inhaled air does not receive any significant amount of exhaled air from the preceding cycle, and rebreathing cycles in which the inhaled air receives an end tidal portion of the exhaled air from the preceding cycle;

(b) measuring the carbon dioxide content in the exhaled air during both the normal breathing cycles and the rebreathing cycles; and (c) utilizing the carbon dioxide content measurements to determine the cardiac output of the subject.

According to further features in this preferred embodiment of the invention described below, the carbon dioxide content is measured without the use of a scrubber by:

(1) measuring the carbon dioxide concentration in the exhaled air during both the normal breathing cycles and the rebreathing cycles;

(2) propagating ultrasonic pulses obliquely through the air passing through the respiratory tube;

(3) measuring the transit times of said pulses;

(4) computing from the measured transit times the flow volume; and (5) multiplying the flow volume by the measured carbon dioxide concentration.

According to still her features in the preferred embodiment of the invention described below, the carbon dioxide concentration is measured by computing from the measured transit times the fraction of carbon dioxide in the exhaled air. More particularly, the carbon dioxide concentration in the exhaled air is computed by:

(i) determining from the measured transit times the oxygen fraction in the inhaled air ($F_IO_2$) and in the exhaled air ($F_EO_2$); and (ii) computing the carbon dioxide content ($VCO_2$) in the exhaled air according to the following equation:

$$VCO_2 = [V_E - (V_E \cdot F_E O_2)] - [V_I - (V_I \cdot F_I O_2)]$$

wherein $V_E$ and $V_I$ are the measured volumes of the inhaled air and exhaled air, respectively.

Thus, the constituents of the exhaled gas, other than nitrogen, oxygen and carbon dioxide, may be ignored. Since carbon dioxide has a substantially higher density than oxygen, and moles of oxygen and carbon dioxide occupy the same volume, it will be seen that the instantaneous carbon dioxide content of the exhaled air may be calculated with a reasonable degree of accuracy simply from the measurements of the mass of the inhaled and exhaled gases. The exhaled $O_2$ concentration $[O_2]_e$ and the exhaled $CO_2$ concentration $[CO_2]_e$ are calculated from the exhaled mass and volume, and, knowing the inhaled $O_2$ concentration $[O_2]_i$, the oxygen volume $[VO_2]$ is then calculated by the following equation:

$$VO_2 = \frac{1 - [O_2]_e - [CO_2]_e}{1 - [O_2]_i} \times ([O_2]_i - [O_2]_e) Vek$$

where k is a non-adiabatic correction constant to compensate for the non-ideal nature of the cases.

The $CO_2$ volume ($VCO_2$) is calculated as:

$$VCO_2 = [CO_2]_e \times Ve$$

Where Ve is the total exhaled volume.

An ultrasonic flow meter, such as described in U.S. Pat. Nos. 4,425,805; 4,914,959 or 5,645,0791, may be used for this purpose. The use of an ultrasonic transit time flow meter for measuring the carbon dioxide content of the exhaled gas avoids the need of a scrubber. It also avoids the need of a capnometer for measuring carbon dioxide concentration, and an oxygen sensor, operating upon the respiratory gasses as they pass through the flow tube, and thereby enables the gasses to pass in a substantially continuous and uninterrupted manner to provide high uniformity in the measurement.

While the preferred embodiment described below utilizes the ultrasonic flow meter to measure flow volume, as well as carbon dioxide and/or oxygen concentration, the described technique may also use a conventional capnometer to sense the carbon dioxide content of the exhaled air, and/or an oxygen sensor for sensing the oxygen content of the exhaled air. The use of an oxygen sensor as an alternative to a capnometer provides the advantages of lower cost, higher reliability, and higher accuracy of the oxygen measurement. It is also contemplated that another type of flow meter may be used, other than the ultrasonic flow meter, but with the carbon dioxide sensor and/or the oxygen sensor.

The described technique may be used not only for non-invasively determining cardiac output, but also for non-invasively determining total oxygen consumption, carbon dioxide production, and other metabolic and/or cardiovascular conditions of the subject by merely analyzing the respiratory gasses produced during breathing in accordance with the techniques described in my above-cited patents.

Further features and advantages of the invention will be apparent from the description below.

BRIEF DESCRIPTION OF THE DRAWINGS

The invention is herein described, by way of example only, with reference to the accompanying drawings, wherein.

DESCRIPTION OF A PREFERRED EMBODIMENT

Figure 1:
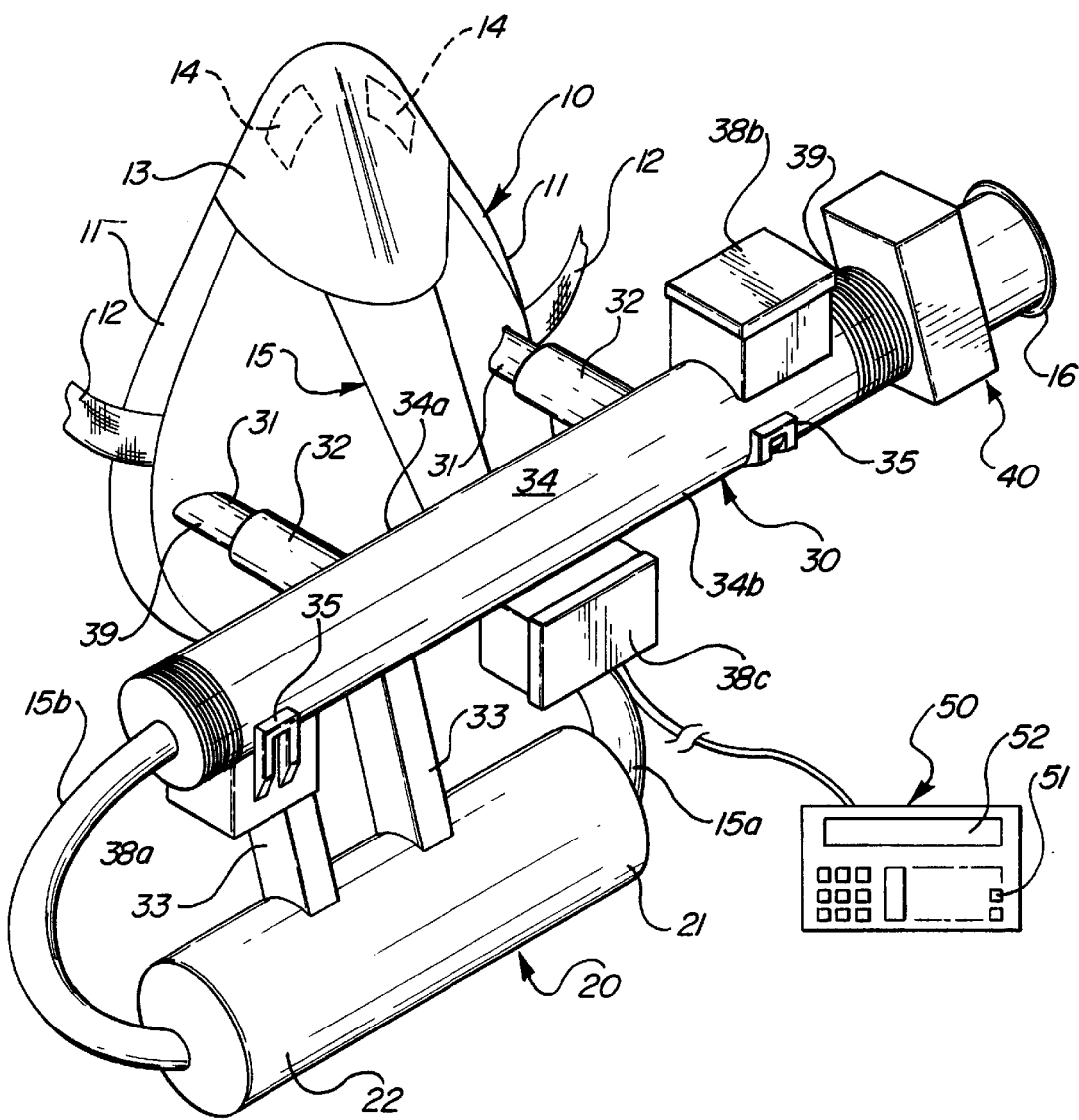
FIG. 1 is a three-dimensional view illustrating one form of apparatus constructed in accordance with the present invention.

The apparatus illustrated in FIG. 1 includes a face mask, generally designated 10, adapted to be applied over a subject's face so as to cover the nose and mouth. Mask 10 has a resilient edge section 11 which engages the subject's face in an airtight manner. The mask may be supported against the subject's face by manually holding it there, but preferably the mask has straps 12 which pass around the rear of the subject's head. The mask could also be retained by a pressure sensitive coating formed on the edge section 11.

Mask 10 is preferably formed of a rigid plastic material, but its nose section 13, intended to enclose the subject's nose, is preferably formed of a more resilient material. Pressure sensitive adhesive pads 14 are formed on the inner surface of the nose section 13, to firmly retain the nose section on the subject's nose, while permitting the subject to breathe freely through the nose.

The interior of mask 10 is connected by a respiratory tube, generally designated 15, to an outer port 16 via: a valve-controlled flow unit, generally designated 20; an ultrasonic flow-measuring unit, generally designated 30, which unit also includes an oxygen sensor; and a capnometer, generally designated 40, for measuring the carbon dioxide concentration in the air passed through the respiratory tube.

The valve-controlled flow unit 20 is described below particularly with reference to FIGS. 2 and 3. Briefly, it includes valve means which may be selectively controlled to convert the flow path through the respiratory tube 15 according to either a first configuration, producing normal breathing cycles in which the inhaled air does not receive any significant amount of exhaled air from the preceding cycle; or to a second configuration, producing rebreathing cycles in which the inhaled air receives an end tidal portion of the exhaled air from the preceding cycle.

The ultrasonic flow-meter unit 30 is more particularly described below with respect to FIG. 4. Briefly, this unit measures the flow velocity through the respiratory tube 15 to its outer port 16, and also enables computing the instantaneous carbon dioxide and/or oxygen content of the air passing through the respiratory tube 15 during inhalations and exhalations therethrough.

The capnometer 40, which measures the instantaneous carbon dioxide concentration in the air passing therethrough, is an optional unit, which may be used instead of the ultrasonic unit 30 for measuring carbon dioxide concentration, or together with the ultrasonic unit 30 in order to increase the precision and reliability of the apparatus.

Figure 2:
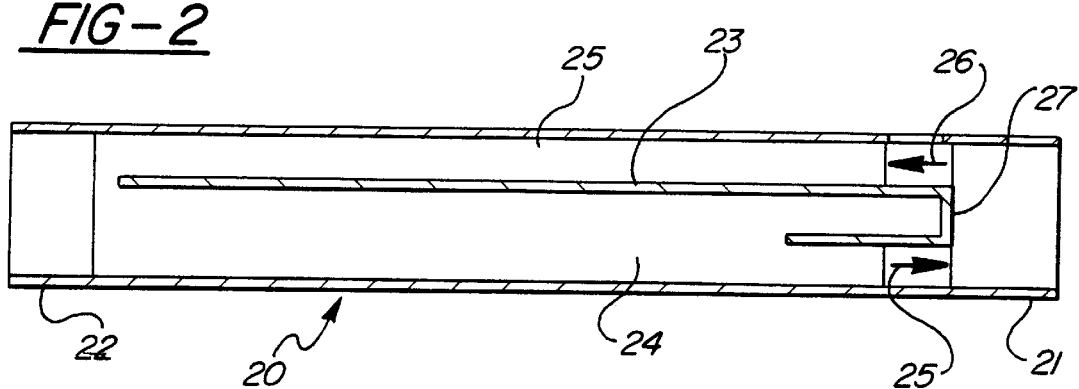
FIG. 2 diagrammatically illustrates the valve-controlled flow unit in the apparatus of FIG. 1, configured for normal breathing cycles.
Figure 3:
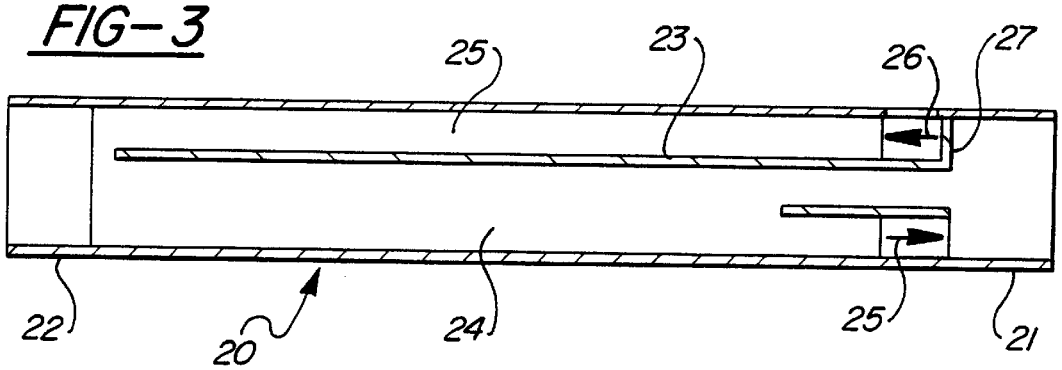
FIG. 3 illustrates the valve-controlled flow unit of FIG. 3, but configured for rebreathing cycles.

The valve-controlled flow unit 20, as illustrated in FIGS. 2 and 3, is of the construction described in my patent application Ser. No. 814,677, now U.S. Pat. No. 5,836,300, except that it omits the scrubber for removing the carbon dioxide from the air stream. This unit, of tubular configuration, is connected at one end 21 to mask 10 via the respiratory tube section 15a, and at the opposite end 22 to the ultrasonic flow meter unit 30 via respiratory tube section 15b. The interior of unit 20 includes a partition 23 which terminates short of the two ends 21, 22, to define two air flow paths 24, 25, through the interior of unit 20 on opposite sides of the partition 23. Flow path 24 is connected to end 21 by a one-way valve 25 permitting air flow only in the inhalation direction (left-to-right, FIG. 2). This end 21 also includes a second one-way valve 26 permitting air flow only in the exhalation direction.

End 21 of unit 20 further includes a valve 27 controlling the air flow at that end of the unit according to its position as illustrated in FIGS. 2 and 3. Thus, when valve 27 is in the position illustrated in FIG. 2, it effects a normal breathing cycle, in which: the inhaled air entering the unit from end 22 flows via path 24 and one-way valve 25 to end 21 of the unit;

and the exhaled air from end 21 passes via one-way valve 26 and flow path 25 to end 22 of the unit. When valve 27 is in the position illustrated in FIG. 3, it closes path 25 to the exhaled air but opens path 24 to the exhaled air.

My patent application Ser. No. 814,677 (now U.S. Pat. No. 5,836,300) more particularly describes the manner in which the FIG. 2 position of valve 27 produces a normal breathing cycle in which the inhaled air does not receive any significant amount of the exhaled air from the preceding cycle, whereas the FIG. 3 position of valve 27 produces a rebreathing cycle in which the inhaled air receives an end tidal portion of the exhaled air from the preceding cycle. That patent application, whose description is hereby incorporated into the present description by reference, also describes how unit 20 is used for measuring the carbon dioxide content of the air passing through that unit, particularly during exhalation, and how these measurements are used during the normal breathing cycles and rebreathing cycles for determining the cardiac output of the subject.

The ultrasonic flow metering unit 30 may be of the construction described in the above-cited U.S. Pat. No. 5,645,071, which description is hereby incorporated by reference. It is supported on mask 10 by a pair of bosses 31 integrally formed in the mask and received within tubular mouthing members 32 integrally formed on unit 30. Unit 30 may also be formed with mounting posts 33 for mounting the rebreathing valve controlled unit 20.

Figure 4:
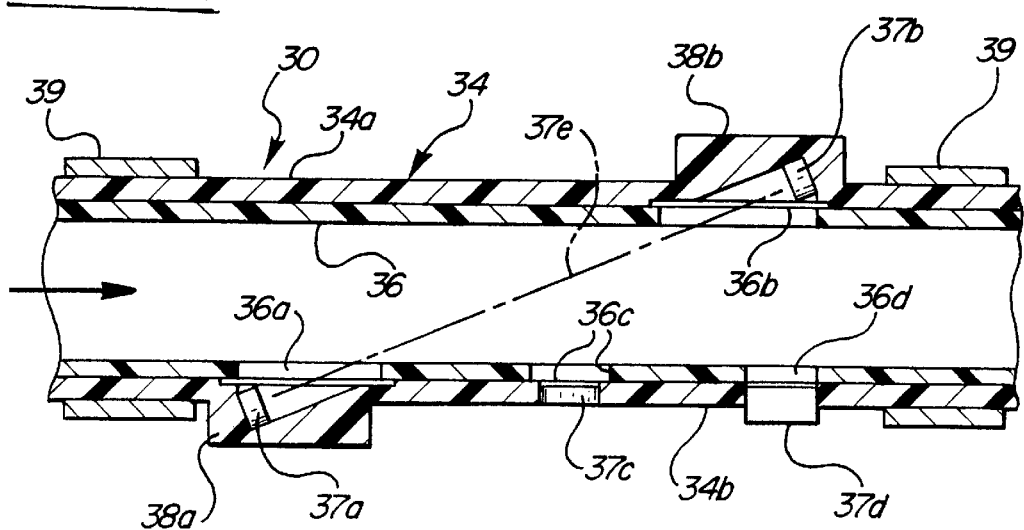
FIG. 4 is a cross-sectional view of the ultrasonic flow meter unit in the apparatus of FIG. 1.

As shown in FIGS. 1 and 4, the ultrasonic flow metering unit 30 includes a tubular housing 34 constituted of two sections 34a, 34b, clamped together by clamps 35 over an inner tube 36. The inner tube 36 is formed with a pair of diametrically-opposed axially-spaced windows 36a, 36b, and the outer housing 34 carries a pair of ultrasonic transceivers 37a, 37b, aligned with these windows and enclosed within housing sections 31a, 38b. The inner tube 36 is formed with a further pair of windows 36c, 36d, and the outer housing 34 carries an oxygen sensor 37c aligned with window 36c, and a temperature sensor 37d aligned with window 36d. These windows may be provided with anti-microbial filters.

Housing 34 further includes an electrical heater 39 at one or both ends of the housing. Housing 34 is further formed with a housing section 38c containing the electronic circuitry which receives the signals from the ultrasonic transducers 37a, 37b, the oxygen sensor 37c, and the temperature sensor 37d. These signals, or information derived from them, are fed to the processor 50, which controls the overall operation of the apparatus as will be described more particularly below. Computer 50 includes a keyboard 51 and display 52. It also receives the carbon dioxide information sensed by the capnometer 40 when included in the apparatus.

OPERATION

The apparatus illustrated in the drawings is used for determining the cardiac output of a subject in the following manner:

The subject is caused to inhale and exhale air via the respiratory tube 15 in a plurality of breathing cycles, including: (a) normal breathing cycles, in which the inhaled air does not receive any significant exhaled air from the preceding cycle; and (b) rebreathing cycles in which the inhaled air receives an end tidal portion of the exhaled air from the preceding cycle. This operation is controlled by the valves within the valve-control flow unit 20 as briefly described above, and as more particularly described in my patent application Ser. No. 814,677, now U.S. Pat. No. 5,836,300, except that the scrubber included in the description of that application is not present here. Rather, the ultrasonic flow metering unit 30 is used for measuring the carbon dioxide content of the exhaled gas in the manner described above, and more particularly described in U.S. Pat. No. 5,645,071, incorporated by reference herein.

For example, a breathing test may take approximately six minutes, of which three minutes is used for normal breathing cycles and three minutes for rebreathing cycles. In the normal breathing cycles, the inhaled air does not receive any significant exhaled air from the preceding cycle, whereas in the rebreathing cycles, the inhaled air receives an end tidal portion of the exhaled air from the preceding cycle.

During each cycle, the subject first inhales air from end 16 of respiratory tube 15, which end may be connected either to the ambient air or to a source of conditioned air as used in a forced respiratory apparatus. During each exhalation, the air is forced from the subject's mask 10 through the respiratory tube 15 to flow through the valve-control flow unit 20 and the ultrasonic flow metering unit 30 and capnometer 40 (if included) out through the outlet 16.

During the flow of the air through the ultrasonic flow metering unit 30, ultrasonic transceiver 37a transmits ultrasonic pulses to transceiver 37b along the line shown at 37e in FIG. 4 which is oblique to the flow path of the air. The transit time of these pulses is a function of both the flow volume through unit 30 and the mass of the gas flowing through that unit, as described in the above-cited U.S. Pat. No. 5,645,071. Processor 50, which receives this information from the transceivers, computes these transit times, and also computes the flow volume and mass of the flowing gas, in the manner described above. Preferably, processor 50 includes counters to determine the transit time of each pulse from its transmitter to its receiver.

The inhaled air is generally of a known composition, typically being, for ambient air, 79% nitrogen, 21% oxygen and 0.03% carbon dioxide. The transit time during inhalations may establish a base against which the transit time during exhalations is compared in order to determine the carbon dioxide content of the exhalation, The temperature of the air passing through unit 30 may be regulated by electrical resistors 39 and measured by temperature sensor 37d, to permit precise computation of the mass and flow volume. The provision of the oxygen sensor 37c and the carbon dioxide sensor 40 also permits precise determination of the flow volume and mass or, alternatively, direct determination of the oxygen and carbon dioxide, using the flow meter to determine flow volumes only.

The manner of utilizing this information for determining cardiac output is more particularly described in my patent application Ser. No. 814,677, now U.S. Pat. No. 5,836,300, as well as in the Capek and Roy publication, identified in column 2, lines 49–55 of that patent, which patent and publication are incorporated herein by reference.

The oxygen consumption is determined by solving the equation $VO_2 = V_I \times (F_I O_2) - V_E \times (F_E O_2)$ where $VO_2$ is the consumed oxygen, $V_I$ is the inhaled volume, $V_E$ is the exhaled volume, $F_I O_2$ is the fraction of oxygen in the inhalation, and $F_E O_2$ is the fraction of oxygen in the exhalation. The system integrates the instantaneous flow volumes with the instantaneous oxygen levels over an entire breathing cycle, which is typically three to ten minutes. The system calculates carbon dioxide production in accordance with the following equation:

$$VCO_2 = [V_E \cdot F_E O_2)] - [V_I \cdot F_I O_2)]$$

Other respiratory parameters such as RQ, REE, etc. may be calculated in the manner disclosed in my previous issued patents.

With the addition of a noninvasive pulse oximeter to measure continuous arterial oxygen saturation, the hemoglobin concentration as well as the pulmonary artery mixed venous saturation may also be determined.

Using the following formulae, the primary measurements of this device (cardiac output, C.O.; oxygen consumption, $VO_2$) and additional $SaO_2$ determined by the pulse oximeter allows measurement of venous oxygen saturation as follows:

$$SvO_2 = \left( \frac{VO_2}{(\text{cardiac output} * \text{hemoglobin} * 1.39)} \right) - SaO_2$$

While the invention has been described with respect to a preferred embodiment, it will be appreciated that this is set forth merely for purposes of example, and that many other variations, modifications and applications of the invention may be made.

What is claimed is:

1. A method for the non-invasive determination of the cardiac output of a subject, comprising:
   (a) causing the subject to inhale air and exhale gas via a respiratory tube in a plurality of breathing cycles including normal breathing cycles in which the inhaled air does not receive any significant amount of exhaled air from the preceding cycle, and rebreathing cycles in which the inhaled air receives an end tidal portion of the exhaled air from the preceding cycle;
   (b) propagating ultrasonic pulses through the air and gas passing through the respiratory tube;
   (c) measuring the transit times of said pulses;
   (d) computing from said measured transit times the flow volumes during inhalation and exhalation;
   (e) using the flow volumes to determine the carbon dioxide content in the exhaled air during both the normal breathing cycles and the rebreathing cycles; and
   (f) utilizing the carbon dioxide content measurements to determine the cardiac output of the subject.

2. The method of claim 1 including measuring the instantaneous values of the carbon dioxide contents of the inhaled and exhaled gases.

3. A method for the non-invasive determination of the cardiac output of a subject, comprising the following steps:
   (a) causing the subject to inhale and exhale air via a respiratory tube in a plurality of breathing cycles including normal breathing cycles in which the inhaled air does not receive any significant amount of exhaled air from the preceding cycle, and rebreathing cycles in which the inhaled air receives an end tidal portion of the exhaled air from the preceding cycle;
   (b) measuring the carbon dioxide content in the exhaled air during both the normal breathing cycles and the rebreathing cycles; and
   (c) utilizing the carbon dioxide content measurements to determine the cardiac output of the subject;
   said carbon dioxide content in the normal breathing cycles and in the rebreathing cycles being measured in step (b) by:
   (1) measuring the carbon dioxide concentration;
   (2) propagating ultrasonic pulses obliquely through the air passing through the respiratory tube;
   (3) measuring the transit times of said pulses;
   (4) computing from said measured transit times the flow volume; and
   (5) multiplying the flow volume by the measured carbon dioxide concentration.

4. The method according to claim 3, wherein said carbon dioxide concentration is measured by computing from said measured transit times the fraction of the carbon dioxide in the exhaled air.

5. The method according to claim 3, wherein said carbon dioxide concentration in the exhaled air is computed by:
   (i) determining from said measured transit times the oxygen fraction in the inhaled air ($F_I O_2$) and in the exhaled air ($F_E O_2$); and
   (ii) computing the carbon dioxide content ($VCO_2$) in the exhaled air according to the following equation:

$$VCO_2 = [V_E - (V_E \cdot F_E O_2)] - [V_I - (V_I \cdot F_I O_2)]$$

wherein $V_E$ and $V_I$ are the measured volumes of the inhaled air and exhaled air, respectively.

6. The method according to claim 5, wherein the temperature of the exhaled air is sensed and is utilized in determining said oxygen fraction.

7. The method according to claim 5, wherein the temperature of the exhaled air is fixed to a predetermined value by an electrical heater.

8. The method according to claim 3, wherein the carbon dioxide concentration is measured by a capnometer.

9. The method according to claim 3, wherein the carbon dioxide concentration is measured by measuring the oxygen concentration in the exhaled air by means of an oxygen sensor, and utilizing said oxygen concentration measurement to determine the carbon dioxide concentration in the exhaled air.

10. The method according to claim 3, wherein the total oxygen consumption during said plurality of breathing cycles is also determined in addition to the subject's cardiac output.

11. The method according to claim 3, wherein the carbon dioxide production during said plurality of breathing cycles is also determined in addition to the subject's cardiac output.

12. Apparatus for the non-invasive determination of the cardiac output of a subject, comprising:
   (a) a respiratory tube adapted to be used by the subject, and defining a flow path for inhaling and exhaling air in a plurality of breathing cycles;
   (b) valve means within said respiratory tube controlling said flow path to convert it to a first configuration producing normal breathing cycles in which the inhaled air does not receive any significant amount of exhaled air from the preceding cycle, or a second configuration producing rebreathing cycles in which the inhaled air receives an end tidal portion of the exhaled air from the preceding cycle;
   (c) ultrasonic pulse means for passing pulses through the respiratory tube and determining the flow volumes through the respiratory tube by measuring the transit times of said pulses;
   (d) measuring means for measuring the carbon dioxide content of the air passing through the flow path; and
   (e) a data processor utilizing the flow volumes and carbon dioxide content measurements to determine the cardiac output of the subject.

13. The apparatus according to claim 12, wherein said data processor computes said carbon dioxide content of the air passing through the flow path by:

(i) determining from measuring transit times of said ultrasonic pulses through the respiratory tube the fraction of oxygen in the inhaled air ($F_IO_2$) and in the exhaled air ($F_EO_2$); and (ii) computing the carbon dioxide content ($VCO_2$) in the exhaled air according to the following equation:

$$VCO_2 = [V_E - (V_E \cdot F_E O_2)] - [V_I - (V_I F_I O_2)]$$

wherein $V_E$ and $V_I$ are the measured volumes of the inhaled air and exhaled air, respectively.

14. The apparatus according to claim 13, wherein the apparatus further includes a temperature sensor for sensing the temperature of the exhaled air, and said data processor utilizes said sensed temperature in determining said oxygen fraction.

15. The apparatus according to claim 14, wherein the apparatus further includes an electrical heater for heating the exhaled air passing through said respiratory tube to a predetermined temperature.

16. The apparatus according to claim 12, wherein said means for measuring the carbon dioxide concentration includes a capnometer.

17. The apparatus according to claim 12, wherein said means for measuring the carbon dioxide concentration includes an oxygen sensor for measuring the oxygen concentration in the exhaled air; said data processor including means for determining from said measured oxygen concentration in the exhaled air, the carbon dioxide concentration in the exhaled air.

18. The apparatus according to claim 12, wherein said data processor also includes means for computing the total oxygen consumption during said plurality of breathing cycles in addition to the subject's cardiac output.

19. The apparatus according to claim 12, wherein said data processor also includes means for computing the total carbon dioxide production during said plurality of breathing cycles in addition to the subject's cardiac output.

* * * * *